United States Patent
Chiu et al.

(10) Patent No.: US 9,394,217 B2
(45) Date of Patent: Jul. 19, 2016

(54) STAGED FLUORINATION PROCESS AND REACTOR SYSTEM

(71) Applicant: Honeywell International, Inc., Morristown, NJ (US)

(72) Inventors: Yuon Chiu, Denville, NJ (US); Haluk Kopkalli, Staten Island, NY (US); Robert A. Smith, Kinnelon, NJ (US); Daniel C. Merkel, Orchard Park, NJ (US)

(73) Assignee: HONEYWELL INTERNATIONAL, INC., Morristown, NJ (US)

(*) Notice: Subject to any disclaimer, the term of this patent is extended or adjusted under 35 U.S.C. 154(b) by 9 days.

(21) Appl. No.: 14/206,100

(22) Filed: Mar. 12, 2014

(65) Prior Publication Data

US 2014/0275648 A1    Sep. 18, 2014

Related U.S. Application Data

(60) Provisional application No. 61/779,625, filed on Mar. 13, 2013.

(51) Int. Cl.
 *C07C 17/00* (2006.01)
 *C07C 17/25* (2006.01)
 *C07C 17/087* (2006.01)

(52) U.S. Cl.
 CPC ............... *C07C 17/25* (2013.01); *C07C 17/087* (2013.01)

(58) Field of Classification Search
 CPC ...... C07C 17/25; C07C 17/087; C07C 19/10; C07C 21/18
 USPC .................................................. 570/156, 168
 See application file for complete search history.

(56) References Cited

U.S. PATENT DOCUMENTS

| | | |
|---|---|---|
| 2009/0240090 A1 | 9/2009 | Merkel et al. |
| 2009/0312585 A1 | 12/2009 | Merkel et al. |
| 2010/0036179 A1 | 2/2010 | Merkel et al. |
| 2010/0048961 A1 | 2/2010 | Merkel et al. |
| 2010/0331583 A1 | 12/2010 | Johnson et al. |
| 2011/0105807 A1 | 5/2011 | Kopkalli et al. |
| 2012/0296128 A1 | 11/2012 | Merkel et al. |

FOREIGN PATENT DOCUMENTS

CN    102001910 A    4/2011

OTHER PUBLICATIONS

International Search Report and Written Opinion corresponding to PCT/US2014/024358, dated Jul. 15, 2014.

*Primary Examiner* — Jafar Parsa
(74) *Attorney, Agent, or Firm* — Scully, Scott, Murphy & Presser

(57) ABSTRACT

The invention relates to a process to produce 244bb from 1233xf in multiple reaction zones whereby the 1233xf starting material is at least 95% converted to 244bb and by-product such as 245cb forms in amounts less than about 2%.

17 Claims, No Drawings

US 9,394,217 B2

STAGED FLUORINATION PROCESS AND REACTOR SYSTEM

FIELD OF THE INVENTION

The present invention relates to a staged fluorination process and reactor system useful in preparing fluorinated organic compounds, particularly 2-chloro-1,1,1,2-tetrafluoropropane (244bb), useful e.g. in processes to make fluorinated olefins, such as 2,3,3,3-tetrafluoropropene (1234yf).

BACKGROUND OF THE INVENTION

Fluorocarbons, particularly fluorinated olefins, as a class, have many and varied uses, including as chemical intermediates and monomers. In particular, these products are useful as refrigerants, monomers or intermediates for preparing refrigerants, particularly those identified as having low global warming potential.

With concerns over global warming, hydrofluoroolefins (HFOs) are being commercialized as substitutes for chlorofluorocarbons (CFCs), hydrochlorofluorocarbons (HCFCs) and hydrofluorocarbons (HFCs) for use as refrigerants, heat transfer agents, blowing agents, monomers and propellants because HFOs do not deplete the ozone layer and have low global warming potential. Some HFOs are prepared by multiple steps that involve fluorinating a chlorinated organic compound with a fluorination agent such as hydrogen fluoride in the presence of a fluorination catalyst. These reactions may be conducted in either the liquid or gas phase or a combination of these. In processes to manufacture 2,3,3,3-tetrafluoropropene (1234yf), the following reaction sequence is known:

Step 1: TCP+3HF→1233xf+3HCl
wherein TCP is 1,1,2,3-tetrachloropropene, or $CCl_2=CClCH_2Cl$; and 1233xf is 2-chloro-3,3,3,-trifluoropropene, or $CH_2=CClCF_3$.

Step 2: 1233xf+HF→244bb
wherein 244bb is 2-chloro-1,1,1,2-tetrafluoropropane, or $CH_3CClFCF_3$.
A by-product of Step 2 can also form as follows: 1233xf+2HF→245cb+HCl, where 245cb is 1,1,1,2,2-pentafluoropropane, or $CH_3CF_2CF_3$.

Step 3: 244bb→1234yf+HCl
wherein 1234yf is 2,3,3,3-tetrafluoropropene, or $CH_2=CFCF_3$.

Whereas, in Step 2, a high conversion of 1233xf concurrent with low selectivity to the 245cb by-product is sought, it has been found, especially when an antimony chloride complex catalyst is used, that less than desirable conversion and selectivity is often obtained. There is thus a need to simultaneously achieve high conversion of 1233xf with low selectivity of 245cb and to gain the resultant economic and commercial benefits in, e.g. the production of 1234yf as a final product.

SUMMARY OF THE INVENTION

The present invention relates, in part, to a process to prepare 244bb comprising contacting 1233xf with HF in the presence of a fluorination catalyst in multiple reaction zones under conditions effective to produce a composition that comprises 244bb and less than about 2% by weight 245cb. In one practice, the composition produced further comprises less than about 5% by weight of unreacted 1233xf. In one practice, more than about 95% of the 1233xf is converted to 244bb. The multiple reaction zones can include multiple reactors, preferably operated in series. In one practice, at least two reactors are employed; in one practice, three reactors are utilized; in one embodiment, the effluent from the first reactor forms the feed for the second reactor, and the effluent from the second reactor forms the feed for the third reactor, and so forth. Intervening processing steps, such as separation steps, e.g. catalyst removal steps and the like, are within the scope of the invention.

DETAILED DESCRIPTION OF THE INVENTION

The foregoing summary and general description of the invention and the ensuing detailed description are exemplary and explanatory and are not restrictive of the invention, as defined in the appended claims. Other features and embodiments and modifications will be apparent from the present description and are within the scope of the invention. The entire contents of U.S. Pat. Nos. 8,258,355, 8,084,653, and US Published Patent Application No. 2007/0197842 are incorporated herein by reference.

The present invention is a process to prepare 2-chloro-1,1,1,2-tetrafluoropropane (244bb). In one embodiment the process comprises contacting 2-chloro-3,3,3,-trifluoropropene (1233xf) with HF in the presence of a fluorination catalyst in multiple reaction zones, preferably operated in series, under conditions effective to produce a composition that comprises 244bb and less than about 2% by weight 1,1,1,2,2-pentafluoropropane (245cb), preferably less than about 1%, more preferably less than about 0.5% 245cb. In one practice, the composition further comprises less than about 5% by weight of unreacted 1233xf, preferably less than about 2%, more preferably less than about 1% by weigh 1233xf. In another practice, more than about 95% of the 1233xf is converted to 244bb, preferably more than about 98% is converted, more preferably more than about 99% is converted. The multiple reaction zones can include multiple reactors, e.g., two or more reactors are employed; in one embodiment, a staged reactor system wherein the reactors are operated in series, wherein the effluent from the first reactor feeds the second reactor and the effluent from the second reactor feeds the third reactor, if present, and so forth. Intervening processing steps, such as separation steps and the like are within the scope of the invention.

In another embodiment, the process to prepare 2-chloro-1,1,1,2-tetrafluoropropane (244bb) comprises contacting 2-chloro-3,3,3,-trifluoropropene (1233xf) and HF in the presence of a first fluorination catalyst in a first reaction zone under conditions effective to produce a first composition comprising 244bb and 1,1,1,2,2-pentafluoropropane (245cb). This first composition is then contacted with HF, which can be fresh HF or preferably carryover HF from the first reactor, or a combination of fresh and carryover HF, in the presence of a second fluorination catalyst in a second reactor zone under conditions effective to produce a second composition comprising 244bb and less than about 2% by weight 245cb relative to said second composition. The first and second fluorination catalysts may be the same or different. Preferably, the second composition further comprises less than about 5% by weight of unreacted 1233xf, i.e., an amount of less than about 5% by weight relative to the second composition. In one practice, more than about 95% of the 1233xf is converted to 244bb.

In yet another embodiment, the process to prepare 2-chloro-1,1,1,2-tetrafluoropropane (244bb) comprises: a) contacting, in a first reactor zone, a feed 2-chloro-3,3,3,-trifluoropropene (1233xf) with a first fluorinating agent, such as HF, in the presence of first fluorination catalyst under conditions effective to produce a first composition comprising: i) a first amount of 2-chloro-1,1,1,2-tetrafluoropropane (244bb), ii) a first amount of 1,1,1,2,2-pentafluoropropane (245cb), and iii) a first amount of unreacted feed 2-chloro-3,3,3,-trifluoropropene (1233xf); b) contacting, in a second reactor zone, the first composition with a second fluorinating catalyst, and optionally HF which can either be freshly fed to the second reactor zone and/or is carryover in whole or in part from the first reactor zone, under conditions effective to produce a second composition comprising: i) a second amount of 2-chloro-1,1,1,2-tetrafluoropropane (244bb), ii) a second amount of 1,1,1,2,2-pentafluoropropane (245cb), and iii) a second amount of unreacted feed 2-chloro-3,3,3,-trifluoropropene (1233xf), wherein said second amount of unreacted feed 2-chloro-3,3,3,-trifluoropropene (1233xf) is less than about 5% by weight of said feed 2-chloro-3,3,3,-trifluoropropene (1233xf), and said second amount of 1,1,1,2,2-pentafluoropropane (245cb) is less than about 2% by weight of said second composition. Preferably, the conversion of feed 1233xf to 244bb in the second composition is more than about 95%.

In the practice of the invention, the reactor zones may be gas phase, or preferably liquid phase. The reaction zones may be comprised of materials suitable for a fluorination reaction. Preferably the reactor zones are constructed from materials resistant to the corrosive effects of hydrogen fluoride (HF) and catalyst, such materials including e.g. Hastalloy, Inconel, Monel. The reactors may be lined with TFE or PFA as known in the art. Preferably, the process is performed at about 70-120° C. and about 50-120 psig.

The fluorination catalysts contemplated by the invention are, without limitation, those known in the art, and are preferably liquid phase fluorination catalysts. A non-exhaustive list of such fluorination catalysts serviceable in the invention include: Lewis acids, transition metal halides, transition metal oxides, Group IVb metal halides, a Group Vb metal halides, or combinations thereof. Non-exclusive examples of liquid phase fluorination catalysts include antimony halide, a tin halide, a tantalum halide, a titanium halide, a niobium halide, and molybdenum halide, an iron halide, a fluorinated chrome halide, a fluorinated chrome oxide or combinations thereof. Specific non-exclusive examples of liquid phase fluorination catalysts are $SbCl_5$, $SbCl_3$, $SbF_5$, $SnCl_4$, $TaCl_5$, $TiCl_4$, $NbCl_5$, $MoCl_6$, $FeCl_3$, a fluorinated species of $SbCl_5$, a fluorinated species of $SbCl_3$, a fluorinated species of $SnCl_4$, a fluorinated species of $TaCl_5$, a fluorinated species of $TiCl_4$, a fluorinated species of $NbCl_5$, a fluorinated species of $MoCl_6$, a fluorinated species of $FeCl_3$, or combinations thereof. Antimony pentachloride, $SbCl_5$, is preferred, with a fluorinated species of $SbCl_5$ more preferred In the practice of the invention, the first fluorination catalyst and the second fluorination catalyst, (and subsequent fluorination catalysts in practices involving more than two reaction zones) may be the same or different. The catalysts can be readily regenerated by any means known in the art if they become deactivated. One suitable method of regenerating the catalyst involves flowing a stream of chlorine through the catalyst. For example, from about 0.002 to about 0.2 lb per hour of chlorine can be added to the liquid phase reaction for every pound of liquid phase fluorination catalyst. This may be done, for example, for from about 1 to about 2 hours or continuously at a temperature of from about 65° C. to about 100° C.

In a preferred practice, the process of the invention is performed in multiple reaction zones comprising a staged reactor system which system itself comprises a first reactor (or multiplicity of first reactors, e.g. operated in series) in which is contacted 1233xf and HF in the presence of an antimony chloride complex catalyst, e.g. a fluorinated species of $SbCl_5$. The first reactor is operated under conditions effective to provide low selectivity to 245cb. Such conditions can include one or more of the following as appropriate: temperature, pressure, HF to organic (e.g. 1233xf and the like) feed ratio, catalyst quantity, catalyst complex or activity states, $Cl_2$ conditioning volume, residence time, degree of mixing, product 244bb recycle (if any) ratio to 1233xf, reactor geometry including length to diameter ratio (L/D), type of reactor employed (e.g. Continuous Stirred Tank Reactor, CSTR) or multi-stage CSTR or plug flow, introduction and/or non-introduction of fresh HF, complete or partial or superheat vaporization of reactor feed, the degree of catalyst refluxing back into the reactor, and the like.

The composition ensuing from the first reactor (first composition) may be a gaseous effluent, and is comprised of unreacted 1233xf, 244bb (the desired product), and a low quantity of 245cb (the undesired by-product), and a quantity of antimony catalyst which may be optionally substantially removed from the composition, is directed to a second reactor or multiplicity of second reactors, e.g. operated in series) in which the composition is contacted with HF, which is either fed to the second reactor and/or carried over from the first reactor in whole or in part, in the presence of a catalyst, which may be the same or different from that in the first reactor, e.g. it can be an antimony chloride complex catalyst, e.g. a fluorinated species of $SbCl_5$, which is either fed to the second reactor and/or carried over from the first reactor in whole or in part.

The second reactor (or multiplicity of second reactors operated in series is operated under conditions effective to convert the unreacted 1233xf to at least 95% (relative to the starting 1233xf fed to the first reactor). The composition ensuing from the second reactor or series of second reactors (second composition) may be a gaseous effluent and is comprised of less than about 5% by weight unreacted 1233xf (relative to the starting 1233xf fed to the first reactor) and less than about 2% by weight of 245cb by-product.

The second reactor is operated under conditions effective to provide the second composition comprising less than about 2% by weight 245cb, such conditions can include one or more of the following as appropriate: temperature, pressure, HF to organic (e.g. unreacted 1233xf present in the first composition and the like) feed ratio, catalyst quantity, catalyst complex or activity states, $Cl_2$ conditioning volume, residence time, degree of mixing, product 244bb recycle (if any) ratio to unreacted 1233xf, reactor geometry including length to diameter ratio (L/D), type of reactor employed (e.g. Continuous Stirred Tank Reactor, CSTR) or multi-stage CSTR or plug flow, introduction and/or non-introduction of fresh HF, complete or partial or superheat vaporization of reactor feed, the degree of catalyst refluxing back into the reactor, and the like.

The process of the invention may be employed, for example, as part of a larger process to make compounds such as 2,3,3,3-tetrafluoropropene (1234yf). For example, the process of the invention can be the second step of the three-step process to make 1234yf as described above. In a preferred embodiment in this regard, the present invention comprises a step of an integrated manufacturing process for making 2,3,3,3-tetrafluoropropene. The preferred starting material for this process is one or more chlorinated compounds according to Formulae I, II and/or III:

$CX_2=CCl-CH_2X$ (Formula I)

$CX_3-CCl=CH2$ (Formula II)

$CX_3-CHCl-CH_2X$ (Formula III)

wherein X is independently selected from F, Cl, Br, and I, provided that at least one X is not fluorine; Preferably, these compounds contain at least one chlorine, more preferably a majority of X is chlorine, and even more preferably all X is chlorine. Preferably, the method generally comprises at least three reaction steps.

Step 1:

In the first step, a starting composition including one or more compounds having Formula (I), (II) or (III), preferably 1,1,2,3-tetrachloropropene (TCP) and/or 1,1,1,2,3-pentachloropropane (240db), reacts with anhydrous HF in a first vapor phase reactor (fluorination reactor) to produce a mixture of 2-chloro-3,3,3-trifluoropropene (1233xf) and HCl. Preferably the reaction occurs in the presence of a catalyst, such as a fluorinated chromium oxide. The reaction is conducted in a first vapor phase reactor, preferably at a reaction temperature of about 200-400° C. and a reaction pressure of about 0-200 psig. The effluent stream exiting the vapor phase reactor may optionally comprise additional components, such as un-reacted HF, heavy intermediates, and HFC-245cb.

In case of a vapor phase process, the reactor is filled with a vapor phase fluorination catalyst. Any fluorination catalysts known in the art may be used in this process. Suitable catalysts include, but are not limited to chromium, aluminum, cobalt, manganese, nickel and iron oxides, hydroxides, halides, oxyhalides, inorganic salts thereof and their mixtures. Combinations of catalysts suitable for the present invention nonexclusively include $Cr_2O_3$, $FeCl_3/C$, $Cr_2O_3/Al_2O_3$, $Cr_2O_3/AlF_3$, $Cr_2O_3/Carbon$, $CoCl_2/Cr_2O_3/Al_2O_3$, $NiCl_2/Cr_2O_3/Al_2O_3$, $COCl_2/AlF_3$, $NiCl_2/AlF_3$ and mixtures thereof. Chromium oxide/aluminum oxide catalysts are described in U.S. Pat. No. 5,155,082 which is incorporated herein by reference. Chromium (III) oxides such as crystalline chromium oxide or amorphous chromium oxide are preferred with amorphous chromium oxide being most preferred. Chromium oxide ($Cr_2O_3$) is a commercially available material which may be purchased in a variety of particle sizes. Fluorination catalysts having a purity of at least 98% are preferred. The fluorination catalyst is present in an excess but in at least an amount sufficient to drive the reaction.

Step 2:

In the second step, the process of the present invention as described herein is employed whereby 1233xf, produced in Step 1, is converted at more than about 95% to 244bb, in multiple reaction zones, with any 245cb by-product being generated at less than about 2% by weight.

Step 3:

In the third step, the 244bb, produced from Step 2 in accordance with the invention, is fed to a second vapor phase reactor (dehydrochlorination reactor) to be dehydrochlorinated to make the desired product 2,3,3,3-tetrafluoropropene (1233yf). This reactor contains a catalyst that can catalytically dehydrochlorinate 244bb to make 1234yf.

The catalysts here may be metal halides, halogenated metal oxides, neutral (or zero oxidation state) metal or metal alloy, or activated carbon in bulk or supported form. When metal halides or metal oxides catalysts are used, preferably mono-, bi-, and tri-valent metal halides, oxide and their mixtures/combinations, and more preferably mono-, and bi-valent metal halides and their mixtures/combinations. Component metals include, but are not limited to, $Cr^{3+}$, $Fe^{3+}$, $Mg^{2+}$, $Ca^{2+}$, $Ni^{2+}$, $Zn^{2+}$, $Pd^{2+}$, $Li^+$, $Na^+$, $K^+$, and $Cs^+$. Component halogens include, but are not limited to, $F^-$, $Cl^-$, $Br^-$, and $I^-$. Examples of useful mono- or bi-valent metal halide include, but are not limited to, LiF, NaF, KF, CsF, $MgF_2$, $CaF_2$, LiCl, NaCl, KCl, and CsCl. Halogenation treatments can include any of those known in the prior art, particularly those that employ HF, $F_2$, HCl, $Cl_2$, HBr, $Br_2$, HI, and $I_2$ as the halogenation source.

When neutral, i.e., zero valent, metals, metal alloys and their mixtures are used. Useful metals include, but are not limited to, Pd, Pt, Rh, Fe, Co, Ni, Cu, Mo, Cr, Mn, and combinations of the foregoing as alloys or mixtures. The catalyst may be supported or unsupported. Useful examples of metal alloys include, but are not limited to, SS 316, Monel 400, Inconel 825, Inconel 600, and Inconel 625.

Preferred catalysts include activated carbon, stainless steel (e.g. SS 316), austenitic nickel-based alloys (e.g. Inconel 625), nickel, fluorinated 10% CsCl/MgO, and 10% CsCl/$MgF_2$. The reaction temperature is preferably about 300-550° C. and the reaction pressure is preferably about 0-150 psig. Preferably, the reactor effluent is fed to a caustic scrubber or to a distillation column to remove the by-product of HCl to produce an acid-free organic product which, optionally, may undergo further purification.

What is claimed is:

1. A process to prepare 2-chloro-1,1,1,2-tetrafluoropropane (244bb) comprising contacting 2-chloro-3,3,3,-trifluoropropene (1233xf) with HF in the presence of a fluorination catalyst in multiple reaction zones under conditions effective to produce a composition that comprises 244bb and less than about 2% by weight 1, 1, 1, 2, 2-pentafluoropropane (245cb).

2. The process of claim 1 wherein the composition produced comprises less than about 1% by weight 245cb.

3. The process of claim 1 wherein the composition produced further comprises less than about 5% by weight of unreacted 1233xf.

4. The process of claim 3 wherein the composition produced further comprises less than about 2% by weight of unreacted 1233xf.

5. The process of claim 1 wherein more than about 95% of the 1233xf is converted to 244bb.

6. The process of claim 5 wherein more than about 98% of the 1233xf is converted to 244bb.

7. The process of claim 1 wherein the multiple reaction zones comprise multiple reactors operated in series.

8. The process of claim 7 wherein the multiple reactors comprise at lease least first and second reactors operated in series.

9. The process of claim 1 wherein the fluorination catalyst is selected from the group consisting of Lewis acids, transition metal halides, transition metal oxides, Group IVb metal halides, a Group Vb metal halides, or combinations thereof.

10. The process of claim 9 wherein the fluorination catalyst is select from the group consisting of $SbCl_5$, $SbCl_3$, $SbF_5$, $SnCl_4$, $TaCl_5$, $TiCl_4$, $NbCl_5$, $MoCl_6$, $FeCl_3$, a fluorinated species of $SbCl_5$, a fluorinated species of $SbCl_3$, a fluorinated species of $SnCl_4$, a fluorinated species of $TaCl_5$, a fluorinated species of $TiCl_4$, a fluorinated species of $NbCl_5$, a fluorinated species of $MoCl_6$, a fluorinated species of $FeCl_3$, or combinations thereof.

11. The process of claim 1 wherein the fluorination catalyst is the same or different in each of the multiple reaction zones.

12. A process to prepare 2-chloro-1,1,1,2-tetrafluoropropane (244bb) comprising:

a) contacting, in a first reaction zone, feed 2-chloro-3,3,3,-trifluoropropene (1233xf) with HF and first fluorination catalyst under conditions effective to produce a first composition comprising unreacted 1233xf, a first amount of 2-chloro-1,1,1,2-tetrafluoropropane (244bb), and a first amount of 1,1,1,2,2-pentafluoropropane (245cb);

b) contacting, in a second reaction zone, the first composition with a second fluorination catalyst under conditions to produce a second composition, wherein the second composition comprises 244bb, and less than about 5% 1233xf by weight relative to the amount of feed 1233xf, and less than about 2% by weight 245cb.

13. The process of claim 12 wherein the second reaction zone is comprised of one or more reactors operated in series.

14. The process of claim 12 wherein the first and the second reaction zones each comprise CSTR reactors.

15. The process of claim 12 wherein said first composition further comprises carryover first fluorination catalyst which is removed from the first composition prior to contacting in said second reaction zone.

16. The process of claim 12 wherein the first and second fluorination catalysts each comprise a fluorinated $SbCl_5$ species.

17. A process to prepare 2,3,3,3-tetrafluoropropene (1234yf) comprising:
  a) providing a starting composition comprising at least one compound having a structure selected from Formula I, II and II:

$$CX_2=CCl-CH_2X \qquad \text{(Formula I)}$$

$$CX_3-CCl=CH2 \qquad \text{(Formula II)}$$

$$CX_3-CHCl-CH_2X \qquad \text{(Formula III)}$$

wherein X is independently selected from F, Cl, Br and I, provided that at least one of X is not F;
  b) contacting said starting composition with HF under conditions effective to produce a first intermediate composition comprising 2-chloro-3,3,3-trifluoropropene (1233xf);
  c) contacting said first intermediate composition comprising 1233xf with HF in the presence of a fluorination catalyst in multiple reaction zones under conditions effective to produce a second intermediate composition comprising 244bb and less than about 2% by weight 1,1,1,2,2-pentafluoropropane (245cb); and
  d) dehydrochlorinating at least a portion of said 244bb to produce a reaction product comprising 1234yf.

\* \* \* \* \*